United States Patent
Fielden et al.

[11] Patent Number: 5,736,354
[45] Date of Patent: Apr. 7, 1998

[54] DETERMINATION OF TOXICITY

[75] Inventors: Peter Robert Fielden, Bury; Richard David Snook, Congleton, both of United Kingdom

[73] Assignee: Yorkshire Water plc, United Kingdom

[21] Appl. No.: 553,466

[22] PCT Filed: Dec. 20, 1993

[86] PCT No.: PCT/GB93/02603

§ 371 Date: Mar. 21, 1996

§ 102(e) Date: Mar. 21, 1996

[87] PCT Pub. No.: WO95/00834

PCT Pub. Date: Jan. 5, 1994

[30] Foreign Application Priority Data

Jun. 18, 1993 [GB] United Kingdom ............ 9312627

[51] Int. Cl.[6] ............... C12Q 1/02; C12Q 1/04; G01N 21/00
[52] U.S. Cl. ............... 435/29; 435/34; 435/4; 435/808; 436/164; 356/4.01; 356/213
[58] Field of Search ............... 435/29, 4, 34, 435/808; 436/164; 356/4.01, 213

[56] References Cited

U.S. PATENT DOCUMENTS

| | | | |
|---|---|---|---|
| 3,959,081 | 5/1976 | Witz et al. | 435/968 |
| 4,808,517 | 2/1989 | Blondin et al. | 435/29 |
| 5,426,035 | 6/1995 | Greene et al. | 435/29 |
| 5,441,873 | 8/1995 | Knight et al. | 435/34 |

FOREIGN PATENT DOCUMENTS

| | | |
|---|---|---|
| 0527099 | 2/1993 | European Pat. Off. |
| 2683632 | 5/1993 | France. |
| 2005018 | 4/1979 | United Kingdom. |
| 9305142 | 3/1993 | WIPO. |

OTHER PUBLICATIONS

Database WPI—Week 9019, Derwent Publications Ltd., London, GB; AN 90-146619 & SU, A, 1 497 218 (Moscow Lomonosov University) 30 Jul. 1989—see abstract.

*Primary Examiner*—Louise Leary
*Attorney, Agent, or Firm*—Renner, Otto, Boisselle & Sklar

[57] ABSTRACT

There is disclosed a method of determining the toxicity of a fluid sample comprising the steps of: (i) mixing the sample with a suspension of light emitting organisms; (ii) monitoring the light output (E) of the mixture continually over a period of time $(t_o - t_n)$ using a photodetector device sensitive to the wave length of the emitted light; and (iii) determining the differential $d(\log E)/dt$ to give a measure of toxicity concentration.

7 Claims, 3 Drawing Sheets

DETERMINATION OF TOXICITY

This invention relates to a method of monitoring the toxicity of a fluid sample by means of measuring the light output of light emitting microorganisms which have been exposed to the sample. The metering and mixing of the sample medium with a fluidic suspension of the said microorganisms is controlled automatically and the resulting light output interpreted using kinetic theory to relate these data to parameters of toxicolo- gical significance, such as the $EC_{50}$ value, and thereby provide a quantitive estimate of the sample toxicity.

A number of procedures for the determination of toxicity using luminescent bacteria are well known. For example, one such procedure involves the addition of a suspension of the bacterium of the genus *Photobacterium Phosphoreum* to a number of serial dilutions of an aqueous sample. Each diluted aliquot is measured in sequence for the light flux due to *P. Phosphoreum* metabolism at two preset time intervals. A blank, containing no portion of the sample is included for comparison. The light emission, sample concentration, and time data are used to estimate parameters of toxicological significance, such as the well known $EC_{50}$, using a predetermined mathematical algorithm. It is well known that such measurements must be carried out at constant temperature, such that the monitoring apparatus supporting the samples and their dilutions is thermostatically controlled. The bacterium being a naturally occurring species in sea water, requires careful adjustment of sample salinity to maintain constant ionic strength, and thereby constant osmotic conditions, throughout the sample dilution aliquots.

Such toxicity testing is usually applied to aqueous samples, where only 0.5 cm$^3$ of sample is required for a typical test. The bacterium is used as a liquid suspension reagent that is generated daily by reconstitution from a freeze-dried standard product. The popular embodiment of such a measurement device relies upon intensive manual manipulation of sample, osmotic adjuster and bacterium suspension aliquots. It is typical for the sample cuvettes to be loaded manually into a detection device sensitive to the wavelength of light emitted from the bacteria in each test suspension. A common feature of these procedures is the problem associated with other properties of the sample solution which interfere with the detection of the emitted light. Examples of such properties include samples which are coloured or turbid. In this way the light emission from the admixture between the test sample and the bacterium suspension reagent may be attenuated and lead to false estimates of sample toxicity. Techniques to overcome the effects of the above mentioned attenuation usually involve additional equipment, such as multichambered measurement cuvette, and additional complexity in respect of the optical measurement apparatus and data interpretation procedures.

The present invention is directed towards toxicity testing, employing the well known principle of utilising light emitting organisms in conjunction with kinetic rate theory to provide a measurement approach that reduces the complexity of the toxicity assay and at the same time enhances measurement precision. A further feature is that the kinetic rate approach affords a superior means of fully automating toxicity testing, based upon light emitting organisms.

According to the present invention there is provided a method of determining the toxicity of a fluid sample comprising the steps of:

(i) mixing the sample with a suspension of light emitting organisms;

(ii) monitoring the light output (E) of the mixture continually over a period of time $(t_o-t_n)$ using a photodetector device sensitive to the wavelength of the emitted light; and (iii) determining the differential $$\frac{d(\log E)}{dt}$$

to give a measure of toxicity concentration.

The method of determining the toxicity of a fluid sample may comprise the further steps of:

(iv) mixing a fluid sample free from toxicity with the solution containing a suspension of light emitting organisms;

(v) monitoring the light output (B) of the mixture continually over a period of time of equal duration to the period $(t_o-t_n)$ to determine the decay in light output due to natural and environmental factors, and (vi) using the values of light output (B) to obtain a corrected light output value (E') for use in step (iii).

The steps (iv) and (v) may be carried out simultaneously with steps (i) and (ii) and corrected values of light output (E') may be obtained by using the equation:

$$E'_t = E_t/B_t \text{ normalised}$$

Alternatively the steps (iv) and (v) may be carried out to give light output values (B1) before steps (i) and (ii) and again after steps (i) and (ii) to give light output values (B2) and wherein corrected values of light output E' are obtained using the equation:

$$E_t = \frac{2E_t}{[(B1_t)\text{normalized} + (B2_t)\text{normalized}]}$$

The light emitting organism may be the bacterium *Photobacterium Phosphoreum*.

The fluid sample may comprise municipal or industrial effluent. A negative value for the differential $d(\log E')/dt$ indicates a concentration of substance toxic to the organism and provides an indicator to possibly unacceptable levels of cocentration.

The invention will be further apparent from the following description with reference to the several figures of the accompanying drawings, which show, by way of example only, one form of apparatus for performing the method thereof.

Figure 1:
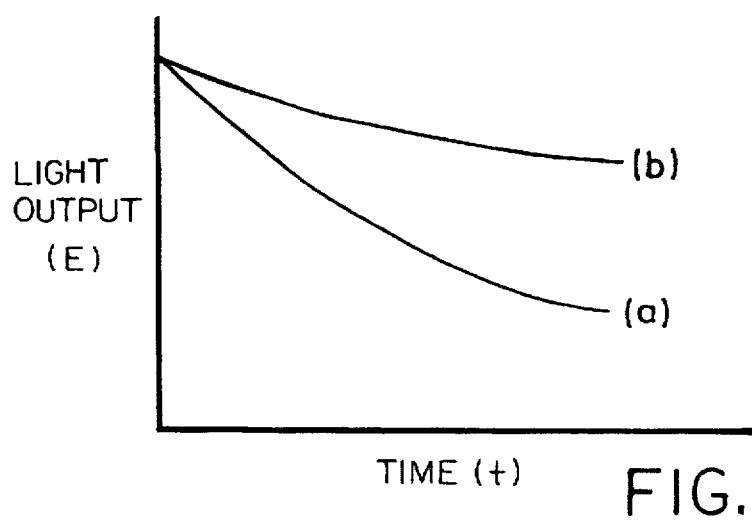
FIG. 1 shows a graph of light output against time illustrating the typical behaviour of light emitting bacteria under toxic load (a) and under blank sample conditions (b)

The method is applied to the toxicity testing of a fluid sample, through admixture with a suspension of light emitting organisms. The emitted light is monitored with respect to time (see FIG. 1) in order to deduce an algorithmic relationship between the decay in light output as a function of both time and sample toxicity, such that sample toxicity may be estimated. The method is based upon the fundamental assumption that during the monitoring period, the concentration, $C_T$, of the toxic agent in any sample remains constant. It is also assumed that the subsequent behaviour of the light emitting organisms may be described by the process:

$$C_T + \text{Organism (Active)} \xrightarrow{K_r} \text{Organism (Dormant)}$$

Figure 2:
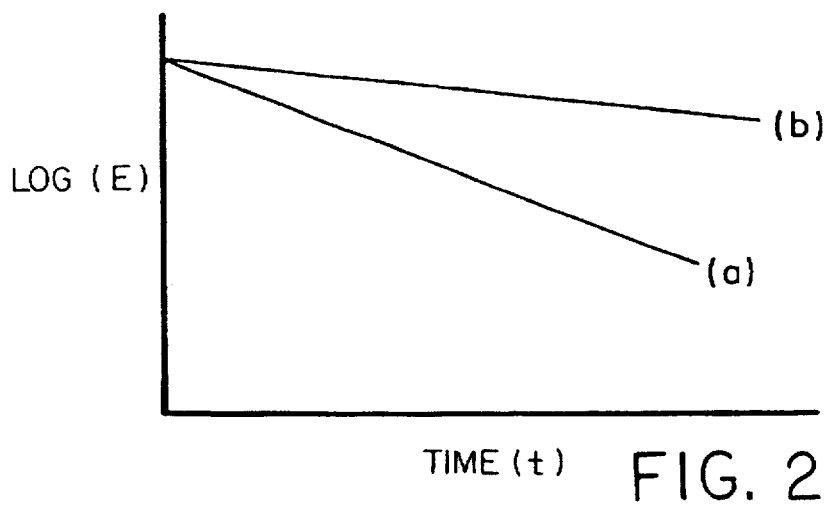
FIG. 2 shows a graph of the logarithm of light output against time again under toxic load (a) and under blank sample conditions (b)

It is also assumed, on the timescale of the typical measurement procedure and over toxic concentration ranges that are not so great as to destroy the organism instantly with respect to that timescale, that the reaction follows pseudo first-order kinetic behaviour, with a rate constant $K_r$, which is independent of the concentration of the organisms in the sample, suspended reagent admixture. The rate equation is well known:

$$K_r = \frac{1}{t} \log \frac{a}{a-x}$$

where t is time, a is the initial light output, and x the decrease in light output. A plot of log (a–x) or (E) against t will yield a straight line of slope $K_r$ (FIG. 2). $K_r$ is related to the reaction half-life, $t_{0.5}$, by $$t_{0.5} = \frac{0.693}{K_r}$$

The reaction half-life corresponds with the $EC_{50}$ condition, and may thereby be deduced through a priori calibration of the measurement with a standardized toxic agent (e.g. 3,5-dichlorophenol). A further feature of the behaviour of light emitting organisms, is that they will exhibit a natural decay in light output even in the absence of a toxic agent. To a first approximation this may be represented by a small negative slope, under the same measurement algorithm as used for toxicity testing, as shown in FIGS. 1b and 2b. This background, or blank decay, may thus be compensated for, to give corrected light emmission values (E') through a process of separate measurement of a standard blank in conjunction with measurement of a sample undergoing toxicity testing.

Figure 3:
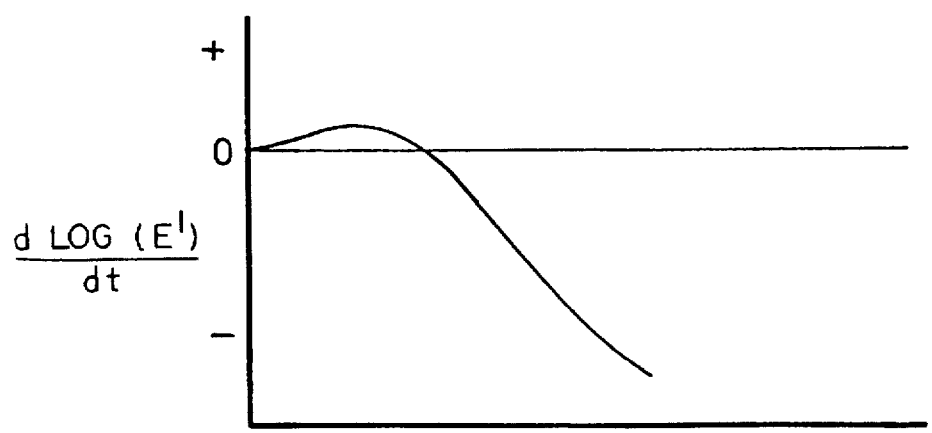
FIG. 3 shows a graph of the slope of plots of the logarithm of corrected light output against time against toxic concentration.

FIG. 3 shows the relationship between the differential $$\frac{d(\log E')}{dt}$$

and toxicity concentration. A negative value for the differential indicates a concentration toxic to the organism and provides an indicator to possibly unacceptable concentrations of toxicity for many requirements.

Figure 4:
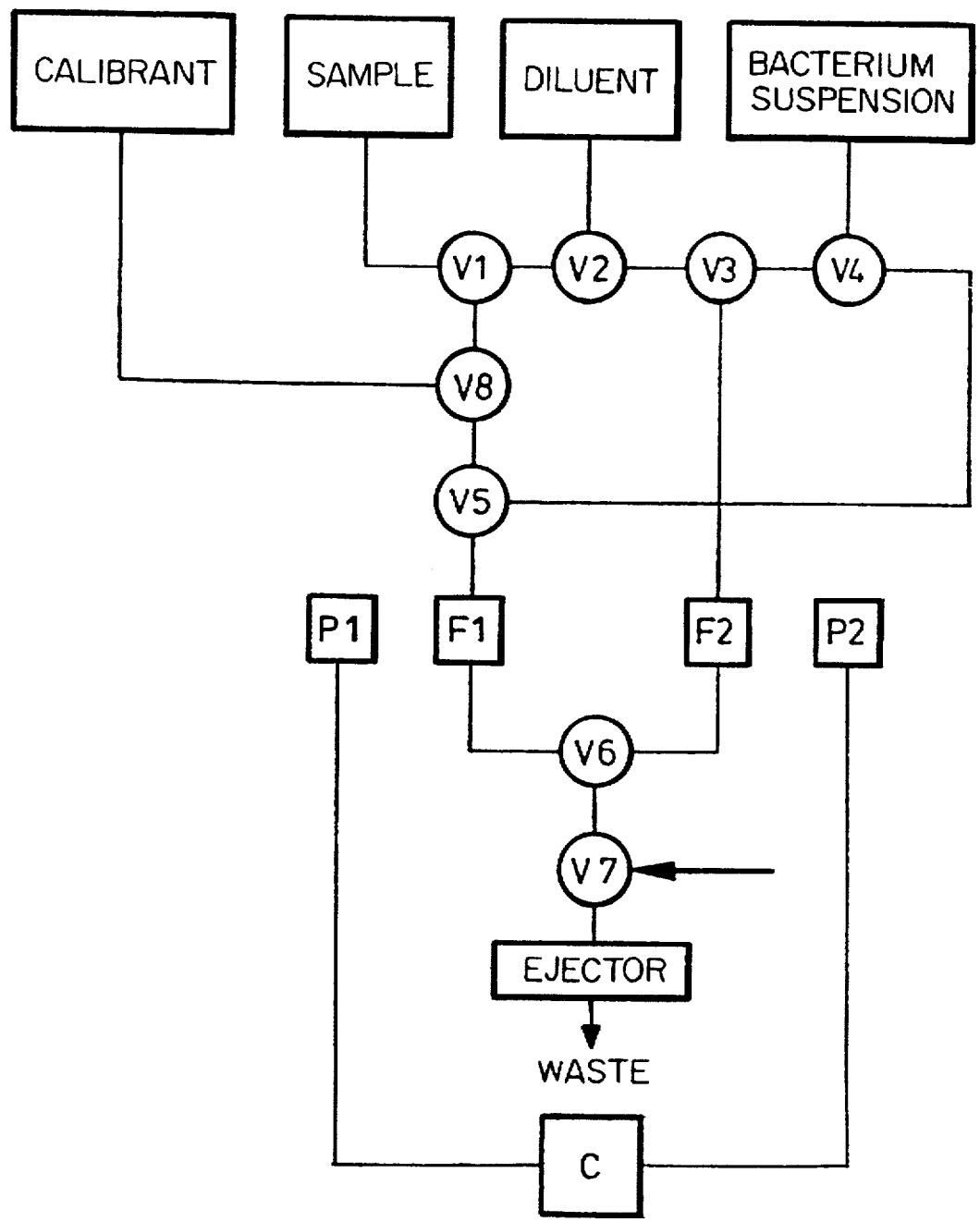
FIG. 4 shows a schematic diagram of the apparatus.

Referring now to FIG. 4, it will be seen that the apparatus essentially comprises a dual channel fluid flow analysis manifold which can receive sample to be tested, a diluent, the bacterium suspension and a calibrant through a series of valves V in required proportions to each of first and second flow cells F1 and F2 monitored by photodetectors P1 and P2 reporting to a microprocessor C.

The sample, either as a continuous stream, as might be obtained from a suitable sampling device, or as a batch sample, which may be delivered manually or as a series of samples by use of an autosampler device for example, is introduced into the flow manifold. The manifold may be constructed from tubes or conduits of a variety of materials with a range of dimensions to control the flow and transport characteristics of the sample introduction. Similarly, the diluent, such as a saline solution, may be added to the sample in a precise way. The sample stream may therefore be transported without modification or with a predetermined dilution factor. The diluent also serves as an inert medium to sequentially carry discrete sample volumes through the manifold. A further feature of the diluent is its application as a blank sample for calibration purposes. Furthermore, excess diluent may be used to flush and thereby wash the manifold between assays and as required. It is evident that although in this example the diluent is multifunctional, it would be possible to introduce further reservoirs, linked with the appropriate valves or diverters, for the operations of blank calibration and washing.

The flow cells should be constructed of material which is transparent to the wavelength of the light emission of the particular microorganisms employed. It is obvious that the flow cell may be of such a volume as to contain the entire admixture or only a portion of the light emission. It is preferred that the admixture is quiescent within the flow cell during the kinetic monitoring period, to maintain best optical precision of the light emission measurement.

The entire manifold, including reagent and sample reservoirs, should be maintained at constant temperature. Any temperature may be utilized, providing that it remains within the operating range of the microorganisms and does not adversely affect liquid viscosity within the manifold. Temperature control may be achieved through any known recognized means.

Although this preferred embodiment utilises liquid transportation through the drawing of liquids through a manifold by means of an ejector, it is clear that many alternatives may be invoked to achieve the said aim of liquid transportation. For example, the liquid reservoirs may be pressurised to force the liquid through the manifold. Alternatively pumping devices may be introduced into some or all of the manifold branches. Furthermore, in miniature form, electroosmotic transport could be utilized. Other embodiments could utilise flow by gravity, capillary action or centrifugal motion.

The outputs from the optical detectors are electronically modified by signal processors to generate a voltage or current suitable for digitisation into the microprocessor. Alternatively analogue computation may be employed, but a digital means is preferred. The entire measurement operation, including selection of manifold configuration within a timed sequence, and monitoring of the function of light emission with time, may all be coordinated using the microprocessor C. The principle of biokinetic monitoring described above, may be implemented through a suitable algorithm introduced into the microprocessor C. In this way a read-out is produced to convey the desired information and measured parameters obtained from the toxic assay operation. Further status information may be advantageously generated for the information of the operator.

Referring to FIG. 5, four possible designs of flow cell are shown. Each flow cell has a liquid input and output, combined with means for interfacing the light emission from the admixture in the cell volume with the optical detectors. The cell shown in FIG. 5(a) comprises a single tube constructed from optically transparent material. The dimensions of length and internal cross-section may be selected to generate a cell volume that is compatible with the admixture volume under study. The cross-section may be of any geometrical design, but circular or rectangular cross-section is preferred.

Figure 5A:
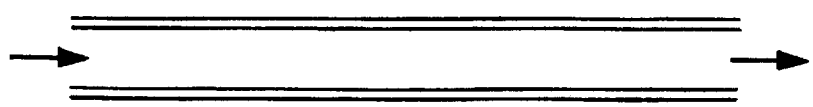
FIG. 5 shows a number of possible flow cell designs for use in the apparatus of FIG. 4.
Figure 5B:
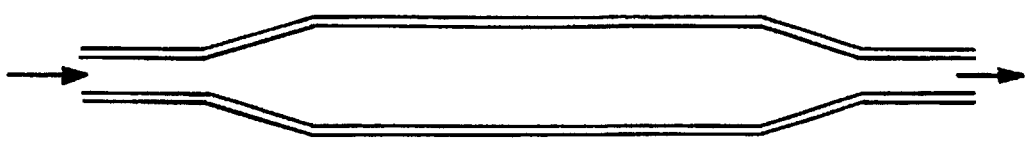

FIG. 5(b) depicts a flow cell, similar to that of FIG. 5(a), but with the addition of a thin layer portion, designed to increase the emission area of the admixture. This design would be particularly appropriate for highly coloured samples, whereby the absorbance path is minimized.

Figure 5C:
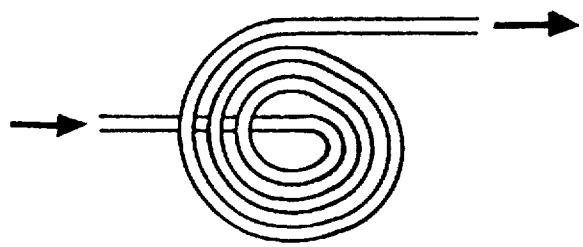

FIG. 5(c) depicts a spiral flow cell, which is based upon the properties of flow cell 5(a). The spiral design enables a greater admixture volume to be maintained within the active area boundary of the optical detection device, whilst maintaining flow in narrow bore tubes. Narrow bore tubes generally maintain the integrity of the admixture plug through reduced dispersion.

Figure 5D:
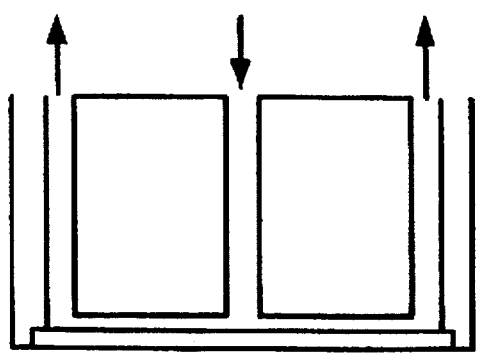

FIG. 5(d) depicts a thin layer wall-jet flow cell, comprising a flat, circular optical window, W1, mounted within a cell body with the means of a narrow bore jet inlet and a low flow restriction output.

Valve V1 selects either pure sample, pure diluent or mixes a controlled portion of sample to form a diluted admixture. Valve V2 diverts diluent to either branch of the dual channel instrument. Valve V3 enables a background admixture, between the bacterium suspension and diluent to be formed. Valve V4 diverts the bacterium suspension to either branch of the dual channel instrument, thus providing luminescent reagent for both toxic and background decay curve monitoring. Valve V5 generates an admixture between the bacterium suspension and either diluent or sample or a sample/diluent admixture. Alternatively, valves V5 and V1 may be deactivated to provide a constant flow between the diluent reservoir and flow cell for the purpose of washing. In a similar fashion, with valve V3 deactivated and valve V2 activated, flow cell 2 may also be washed. Valve V6 selects the outflow from either flow cell 1 or flow cell 2. Valve V7 enables the selection of either the flow cell effluent, or an input of ambient air. This enables the manifold flow to be halted for extended periods, as required. An ejector, powered either from a water or air source, provides the preferred means of drawing liquids through the manifold, and in conjunction with any flow pattern that is set up through the control of the diverter valves. Valve V8 enables introduction of a calibrant.

Detectors P1 and P2 monitor the light emission (E) from the sample under test and that (B) from an admixture of diluent and bacterium suspension alone to determine the background decay of light emission.

The microprocessor C computes corrected values E' using the formula:

$$E'_t = \frac{E_t}{B_t \text{ normalized}}$$

The values B are normalised by dividing all data points by the first data point in the sequence.

The differential $$\frac{d(\log E')}{dt}$$

is then calculated to give a measure of toxicity.

In many applications if the value of the differential is negative that is indicative of an unacceptable level of toxicity and an alarm signal may be generated.

It will be appreciated that it is not intended to limit the invention to the above example only, many variations, such as might readily occur to one skilled in the art, being possible, without departing from the scope thereof as defined by the appended claims.

We claim:

1. A method of determining the toxicity of a fluid sample comprising the steps of:
   (i) mixing the sample with a suspension of light emitting microorganisms;
   (ii) monitoring the light output (E) of the mixture continually over a period of time $(t_o\text{-}t_n)$ using a photodetector device sensitive to the wavelength of the emitted light; and
   (iii) determining the differential $d(\log E)/dt$ to give a measure of toxicity concentration.

2. The method of determining the toxicity of a fluid sample according to claim 1 further comprising the steps of:
   (iv) mixing a fluid sample free from toxicity with the solution containing a suspension of the light emitting microorganisms;
   (v) monitoring the light output (B) of the mixture continually over a period of time of equal duration to the period $(t_o\text{-}t_n)$ to determine the decay in light output due to natural and environmental factors, and
   (vi) using the values of light output (B) to obtain a corrected light output value (E') for use in step (iii).

3. The method according to claim 2 wherein steps (iv) and (v) are carried out simultaneously with steps (i) and (ii) and wherein corrected values of light output (E') are obtained by using the equation:

$$E'_t = E_t/B_{t, \text{ normalised}}.$$

4. The method according to claim 2 wherein steps (iv) and (v) are carried out to give light output values (B1) before steps (i) and (ii) and again after steps (i) and (ii) to give light output values (B2) and wherein corrected values of light output E' are obtained using the equation:

$$E'_t = \frac{2E_t}{[(B1_t)\text{normalized} + (B2_t)\text{normalized}]}.$$

5. The method according to claim 1 wherein the light emitting microorganism is the bacterium *Photobacterium phosphoreum*.

6. The method according to claim 5 wherein the fluid sample comprises municipal or industrial effluent and wherein an unacceptable level of toxicity is recognized by a negative value for the differential $$\frac{d(\log E)}{dt} \text{ or } \frac{d(\log E')}{dt}.$$

7. The method according to claim 2 wherein the light emitting organism is the bacterium *Photobacterium phosphoreum*.

* * * * *